(12) United States Patent
Malhi (10) Patent No.: US 9,956,325 B2
(45) Date of Patent: May 1, 2018

(54) ORIENTATION INDEPENDENT CANISTER FOR A NEGATIVE PRESSURE WOUND THERAPY DEVICE

(71) Applicant: Smith & Nephew, Inc., Memphis, TN (US)

(72) Inventor: Arnaz Malhi, Watertown, MA (US)

(73) Assignee: Smith & Nephew, Inc., Memphis, TN (US)

( * ) Notice: Subject to any disclaimer, the term of this patent is extended or adjusted under 35 U.S.C. 154(b) by 886 days.

(21) Appl. No.: 14/043,529

(22) Filed: Oct. 1, 2013

(65) Prior Publication Data

US 2014/0128822 A1    May 8, 2014

Related U.S. Application Data

(63) Continuation of application No. 13/476,255, filed on May 21, 2012, now Pat. No. 8,568,386, which is a
(Continued)

(51) Int. Cl.
*A61M 1/00* (2006.01)
*A61F 13/00* (2006.01)
(Continued)

(52) U.S. Cl.
CPC ..... *A61M 1/0001* (2013.01); *A61F 13/00068* (2013.01); *A61M 1/0023* (2013.01);
(Continued)

(58) Field of Classification Search
CPC ........ A61M 1/00; A61M 13/02; A61M 27/00; A61F 13/00; A61B 17/50
See application file for complete search history.

(56) References Cited

U.S. PATENT DOCUMENTS 3,367,332 A   2/1968   Groves
3,486,504 A   12/1969  Austin, Jr.
(Continued)

FOREIGN PATENT DOCUMENTS

DE   41 11 122 A1   4/1993
DE   295 04 378 U1  10/1995
(Continued)

OTHER PUBLICATIONS

US 6,216,701, 04/2001, Heaton et al. (withdrawn)
(Continued)

*Primary Examiner* — Michele M Kidwell
*Assistant Examiner* — Ilya Treyger
(74) *Attorney, Agent, or Firm* — Knobbe, Martens, Olson & Bear, LLP (57) ABSTRACT

A portable negative pressure wound therapy system includes a dressing assembly for positioning over a wound to apply a negative pressure to the wound and a canister assembly. The canister assembly includes a control unit having a vacuum source and a controller and a collection canister in communication with the dressing assembly operable to receive fluid from the wound. The collection canister has a filter assembly having a filter and a passageway between the filter and a wall of the collection canister. The collection canister also includes a canister interface having a suction port, an inlet port, and a channel. The vacuum source draws air through the suction port from the channel which draws air from the passageway connected to the channel, the air in the passageway is drawn from the collection canister through the filter, and the air in the collection canister is drawn through the inlet port.

10 Claims, 7 Drawing Sheets

Related U.S. Application Data continuation of application No. 12/463,563, filed on May 11, 2009, now Pat. No. 8,251,979.

(51) Int. Cl.
   *A61M 13/00* (2006.01)
   *A61M 27/00* (2006.01)
   *A61B 17/50* (2006.01)

(52) U.S. Cl.
   CPC ........ A61M 1/0031 (2013.01); A61M 1/0088 (2013.01); *A61M 2209/088* (2013.01); *Y10T 29/49826* (2015.01); *Y10T 137/6055* (2015.04); *Y10T 137/789* (2015.04)

(56) References Cited

U.S. PATENT DOCUMENTS

| | | | |
|---|---|---|---|
| 3,572,340 A | 3/1971 | Lloyd et al. | |
| 3,712,298 A | 1/1973 | Snowdon et al. | |
| 3,809,086 A | 5/1974 | Schachet et al. | |
| 3,874,387 A | 4/1975 | Barbieri | |
| 4,080,970 A | 3/1978 | Miller | |
| 4,112,947 A | 9/1978 | Nehring | |
| 4,112,949 A | 9/1978 | Rosenthal et al. | |
| 4,136,696 A | 1/1979 | Nehring | |
| 4,266,545 A | 5/1981 | Moss | |
| 4,382,441 A | 5/1983 | Svedman | |
| 4,524,064 A | 6/1985 | Nambu | |
| 4,743,232 A | 5/1988 | Kruger | |
| 4,969,880 A | 11/1990 | Zamierowski | |
| 4,990,137 A | 2/1991 | Graham | |
| 4,997,438 A | 3/1991 | Nipper | |
| 5,071,409 A | 12/1991 | Rosenberg | |
| 5,100,395 A | 3/1992 | Rosenberg | |
| 5,100,396 A | 3/1992 | Zamierowski | |
| 5,106,629 A | 4/1992 | Cartmell et al. | |
| 5,141,503 A | 8/1992 | Sewell, Jr. | |
| 5,149,331 A | 9/1992 | Ferdman et al. | |
| 5,152,757 A | 10/1992 | Eriksson | |
| 5,156,602 A | 10/1992 | Steffler | |
| 5,160,322 A | 11/1992 | Scheremet et al. | |
| 5,176,663 A | 1/1993 | Svedman et al. | |
| 5,178,157 A | 1/1993 | Fanlo | |
| 5,195,977 A | 3/1993 | Pollitt | |
| 5,261,893 A | 11/1993 | Zamierowski | |
| 5,263,922 A | 11/1993 | Sova et al. | |
| D364,679 S | 11/1995 | Heaton et al. | |
| 5,484,427 A | 1/1996 | Gibbons | |
| 5,527,293 A | 6/1996 | Zamierowski | |
| 5,536,233 A | 7/1996 | Khouri | |
| 5,549,584 A | 8/1996 | Gross | |
| 5,588,958 A | 12/1996 | Cunningham et al. | |
| 5,636,643 A | 6/1997 | Argenta et al. | |
| 5,645,081 A | 7/1997 | Argenta et al. | |
| 5,678,564 A | 10/1997 | Lawrence et al. | |
| 5,701,917 A | 12/1997 | Khouri | |
| 5,733,305 A | 3/1998 | Fleischmann | |
| 5,840,049 A | 11/1998 | Tumey et al. | |
| 5,911,222 A | 6/1999 | Lawrence et al. | |
| 5,944,703 A | 8/1999 | Dixon et al. | |
| 6,010,524 A | 1/2000 | Fleischmann | |
| 6,071,267 A | 6/2000 | Zamierowski | |
| 6,117,111 A | 9/2000 | Fleischmann | |
| 6,135,116 A | 10/2000 | Vogel et al. | |
| D434,150 S | 11/2000 | Turney et al. | |
| 6,142,982 A | 11/2000 | Hunt et al. | |
| 6,174,306 B1 | 1/2001 | Fleischmann | |
| 6,203,563 B1 | 3/2001 | Fernandez | |
| 6,261,276 B1 | 7/2001 | Reitsma | |
| 6,325,788 B1 | 12/2001 | McKay | |
| 6,345,623 B1 | 2/2002 | Heaton et al. | |
| 6,348,423 B1 | 2/2002 | Griffiths et al. | |
| 6,398,767 B1 | 6/2002 | Fleischmann | |
| 6,406,447 B1 | 6/2002 | Thrash et al. | |
| 6,420,622 B1 | 7/2002 | Johnston et al. | |
| 6,458,109 B1 | 10/2002 | Henley et al. | |
| 6,488,643 B1 | 12/2002 | Tumey et al. | |
| 6,500,112 B1 | 12/2002 | Khouri | |
| D469,175 S | 1/2003 | Hall et al. | |
| D469,176 S | 1/2003 | Hall et al. | |
| 6,520,982 B1 | 2/2003 | Boynton et al. | |
| 6,553,998 B2 | 4/2003 | Heaton et al. | |
| D475,134 S | 5/2003 | Randolph | |
| 6,557,704 B1 | 5/2003 | Randolph | |
| D478,659 S | 8/2003 | Hall et al. | |
| 6,607,495 B1 | 8/2003 | Skalak et al. | |
| 6,626,891 B2 | 9/2003 | Ohmstede | |
| 6,648,862 B2 | 11/2003 | Watson | |
| 6,685,681 B2 | 2/2004 | Lockwood et al. | |
| 6,695,823 B1 | 2/2004 | Lina et al. | |
| 6,695,824 B2 | 2/2004 | Howard et al. | |
| D488,558 S | 4/2004 | Hall | |
| 6,752,794 B2 | 6/2004 | Lockwood et al. | |
| 6,755,807 B2 | 6/2004 | Risk, Jr. et al. | |
| 6,764,462 B2 | 7/2004 | Risk, Jr. et al. | |
| 6,767,334 B1 | 7/2004 | Randolph | |
| 6,800,074 B2 | 10/2004 | Henley et al. | |
| 6,814,079 B2 | 11/2004 | Heaton et al. | |
| 6,824,533 B2 | 11/2004 | Risk, Jr. et al. | |
| 6,855,135 B2 | 2/2005 | Lockwood et al. | |
| 6,856,821 B2 | 2/2005 | Johnson | |
| 6,887,228 B2 | 5/2005 | McKay | |
| 6,887,263 B2 | 5/2005 | Bleam et al. | |
| 6,936,037 B2 | 8/2005 | Bubb et al. | |
| 6,942,633 B2 | 9/2005 | Odland | |
| 6,942,634 B2 | 9/2005 | Odland | |
| 6,951,553 B2 | 10/2005 | Bubb et al. | |
| 6,960,181 B2 | 11/2005 | Stevens | |
| 6,979,324 B2 | 12/2005 | Bybordi et al. | |
| 6,994,702 B1 | 2/2006 | Johnson | |
| 7,022,113 B2 | 4/2006 | Lockwood et al. | |
| 7,037,254 B2 | 5/2006 | O'Connor et al. | |
| 7,052,167 B2 | 5/2006 | Vanderschuit | |
| 7,070,584 B2 | 7/2006 | Johnson et al. | |
| 7,077,832 B2 | 7/2006 | Fleischmann | |
| 7,108,683 B2 | 9/2006 | Zamierowski | |
| 7,117,869 B2 | 10/2006 | Heaton et al. | |
| 7,128,719 B2 | 10/2006 | Rosenberg | |
| 7,128,735 B2 | 10/2006 | Weston | |
| 7,144,390 B1 | 12/2006 | Hanningan et al. | |
| 7,169,151 B1 | 1/2007 | Lytinas | |
| 7,182,758 B2 | 2/2007 | McCraw | |
| 7,195,624 B2 | 3/2007 | Lockwood et al. | |
| 7,198,046 B1 | 4/2007 | Argenta et al. | |
| 7,214,202 B1 | 5/2007 | Vogel et al. | |
| 7,216,651 B2 | 5/2007 | Argenta et al. | |
| D544,092 S | 6/2007 | Lewis | |
| 7,273,054 B2 | 9/2007 | Heaton et al. | |
| 7,276,051 B1 | 10/2007 | Henley et al. | |
| 7,279,612 B1 | 10/2007 | Heaton et al. | |
| 7,316,672 B1 | 1/2008 | Hunt et al. | |
| D565,177 S | 3/2008 | Locke et al. | |
| 7,338,482 B2 | 3/2008 | Lockwood et al. | |
| 7,351,250 B2 | 4/2008 | Zamierowski | |
| 7,361,184 B2 | 4/2008 | Joshi | |
| 7,381,211 B2 | 6/2008 | Zamierowski | |
| 7,381,859 B2 | 6/2008 | Hunt et al. | |
| 7,396,345 B2 | 7/2008 | Knighton et al. | |
| 7,410,495 B2 | 8/2008 | Zamierowski | |
| 7,413,570 B2 | 8/2008 | Zamierowski | |
| 7,413,571 B2 | 8/2008 | Zamierowski | |
| 7,422,576 B2 | 9/2008 | Boynton et al. | |
| 7,569,742 B2 | 8/2009 | Haggstrom et al. | |
| 7,625,362 B2 | 12/2009 | Boehringer et al. | |
| 7,699,823 B2 | 4/2010 | Haggstrom et al. | |
| 7,846,141 B2 | 12/2010 | Weston | |
| 7,909,805 B2 | 3/2011 | Weston | |
| 8,062,272 B2 | 11/2011 | Weston | |
| 8,172,817 B2 * | 5/2012 | Michaels | G01F 23/0053 604/317 |
| 8,177,763 B2 * | 5/2012 | Wiesner | A61M 1/0049 604/313 |
| 8,251,979 B2 | 8/2012 | Malhi | |
| 8,568,386 B2 | 10/2013 | Malhi | |

(56) References Cited

U.S. PATENT DOCUMENTS

| | | |
|---|---|---|
| 9,211,486 B2 | 12/2015 | Locke et al. |
| 2001/0031943 A1 | 10/2001 | Urie |
| 2001/0043943 A1 | 11/2001 | Coffey |
| 2002/0016577 A1 | 2/2002 | Ohmstede |
| 2002/0143286 A1 | 10/2002 | Tumey |
| 2002/0151836 A1 | 10/2002 | Burden |
| 2003/0093041 A1 | 5/2003 | Risk, Jr. et al. |
| 2003/0208149 A1 | 11/2003 | Coffey |
| 2003/0212357 A1 | 11/2003 | Pace |
| 2003/0212359 A1 | 11/2003 | Butler |
| 2003/0219469 A1 | 11/2003 | Johnson et al. |
| 2004/0006319 A1 | 1/2004 | Lina et al. |
| 2004/0030304 A1 | 2/2004 | Hunt et al. |
| 2004/0039415 A1 | 2/2004 | Zamierowski |
| 2004/0064132 A1 | 4/2004 | Boehringer |
| 2004/0093026 A1 | 5/2004 | Weidenhagen et al. |
| 2004/0122434 A1 | 6/2004 | Argenta et al. |
| 2004/0193218 A1 | 9/2004 | Butler |
| 2004/0241213 A1 | 12/2004 | Bray |
| 2004/0243073 A1 | 12/2004 | Lockwood et al. |
| 2005/0010153 A1 | 1/2005 | Lockwood et al. |
| 2005/0020955 A1 | 1/2005 | Sanders et al. |
| 2005/0070835 A1 | 3/2005 | Joshi |
| 2005/0070858 A1 | 3/2005 | Lockwood et al. |
| 2005/0085795 A1 | 4/2005 | Lockwood et al. |
| 2005/0090787 A1 | 4/2005 | Risk, Jr. et al. |
| 2005/0177190 A1 | 8/2005 | Zamierowski |
| 2005/0182445 A1 | 8/2005 | Zamierowski |
| 2005/0222527 A1 | 10/2005 | Miller et al. |
| 2005/0261643 A1 | 11/2005 | Bybordi et al. |
| 2006/0015087 A1 | 1/2006 | Risk, Jr. et al. |
| 2006/0039742 A1 | 2/2006 | Cable, Jr. et al. |
| 2006/0041247 A1 | 2/2006 | Petrosenko et al. |
| 2006/0079852 A1 | 4/2006 | Bubb et al. |
| 2006/0100586 A1 | 5/2006 | Karpowicz et al. |
| 2006/0100594 A1 | 5/2006 | Adams et al. |
| 2006/0116620 A1 | 6/2006 | Oyaski |
| 2006/0149170 A1 | 7/2006 | Boynton et al. |
| 2007/0005028 A1 | 1/2007 | Risk, Jr. et al. |
| 2007/0014837 A1 | 1/2007 | Johnson et al. |
| 2007/0021697 A1 | 1/2007 | Ginther et al. |
| 2007/0027414 A1 | 2/2007 | Hoffman et al. |
| 2007/0032754 A1 | 2/2007 | Walsh |
| 2007/0032755 A1 | 2/2007 | Walsh |
| 2007/0032778 A1 | 2/2007 | Heaton et al. |
| 2007/0055209 A1 | 3/2007 | Patel et al. |
| 2007/0167927 A1 | 7/2007 | Hunt et al. |
| 2007/0179460 A1 | 8/2007 | Adahan |
| 2007/0185426 A1 | 8/2007 | Ambrosio et al. |
| 2008/0071235 A1 | 3/2008 | Locke et al. |
| 2008/0082059 A1 | 4/2008 | Fink et al. |
| 2008/0200857 A1 | 8/2008 | Lawhorn |
| 2008/0200906 A1 | 8/2008 | Sanders et al. |
| 2008/0208147 A1 | 8/2008 | Argenta et al. |
| 2008/0234641 A1 | 9/2008 | Locke et al. |

FOREIGN PATENT DOCUMENTS

| | | |
|---|---|---|
| EP | 0 020 662 | 7/1984 |
| EP | 358 302 | 3/1990 |
| EP | 0 853 950 | 7/1998 |
| GB | 1 549 756 | 3/1977 |
| GB | 2 195 255 A | 4/1988 |
| GB | 2 235 877 A | 3/1991 |
| SU | 1762940 | 1/1989 |
| WO | WO 80/01139 | 6/1980 |
| WO | WO 80/02182 | 10/1980 |
| WO | WO 84/01904 | 5/1984 |
| WO | WO 89/05133 | 6/1989 |
| WO | WO 90/11795 | 10/1990 |
| WO | WO 92/19313 | 11/1992 |
| WO | WO 96/05873 | 2/1996 |
| WO | WO 03/057307 | 7/2003 |
| WO | WO 03/101508 | 12/2003 |
| WO | WO 2005/009488 | 2/2005 |
| WO | WO 2009/124125 | 10/2009 |

OTHER PUBLICATIONS

US 7,186,244, 03/2007, Hunt et al. (withdrawn)
International Search Report for PCT/US2010/034287, dated Jul. 8, 2010.
Bagautdinov, N.A., "Variant of External Vacuum Aspiration in the Treatment of Purulent Diseases of Soft Tissues," in current Problems in Modern Clinical Surgery: Interdepartmental Collection, edited by V. Ye. Volkov et al. (Chuvashia State University, Cheboksary, USSR 1986) pp. 94-96 (with English translation).
Bjorn, et al., "Irrigation Treatment in Split-thickness Skin Grafting of Intractable Leg Ulcers," Scand J Plast Reconstr Surg 19: 211-213,1985.
Chariker, M.E., et al, "Effective Management of Incisional and Cutaneous Fistulae with Closed Suction Wound Drainage," Contemporary Surgery. Jun. 1989, pp. 59-63, vol. 34 USA.
Fleischmann, "Vacuum Sealing for Treatment of Problematical Wounds", University Surgical Clinic and Polyclinic—Accident Surgery Department, WundForum Spezial-IHW 94.
Fleischmann, et al., Vacuum Sealing: Indication, Technique and Results, Emr J Orthop Surg Tramatol (1995) 5:37-40.
Gorica Zivadinovic, et al., "Vacuum Therapy in the Treatment of Peripheral Blood Vessels," Conference Papers of the 5th Timok Medical Days, Majdanpek, 1986 (161-164).
Deter, Katherine F., et al., "Managing Draining Wounds and Fistulae: New and Established Methods", Chronic Wound Care, 1990, pp. 240-246.
Kostiuchenok, et al., "The Vacuum Effect in the Surgical Treatment of Purulent Wounds," Russian Journal: Vestnik Khirurgii, Sep. 1986, (18-21).
Meyer, MD., et al., "In Surgery, Medicine and the Specialties a Manual of its Practical Application", Bier's Hyperemic Treatment, Second Revised Edition, W.B. Saunders Company, 1909.
Mulder, GD, et al., "Clinicians' Pocket Guide to Chronic Wound Repair," Wound Healing Publications Second Edition, 1991.
Ryosuke Fujimoro, MD., et al., "Sponge Fixation Method for Treatment of Early Scars," From the Department of Dermatology in the Faculty Medicine, Kyoto University, vol. 42, No. 4, Oct. 1968 (323-326).
Sandén, Göran MD., et al., "Staphylococcal Wound Infection in the Pig: Part II. Innoculation, Quantification of Bacteria, and Reproducibility," Annals of Plastic Surgery, vol. 23, No. 3, Sep. 1989, (219-223).
Stoll, "Energetic Remedies—Cupping: Healing Within a Vacuum," https://www.suite101.com/article.cfm/ energetic)remedies/74531, Apr. 13, 2005.
Svedman, "A Dressing Allowing Continuous Treatment of a Biosurface," IRCS Medical Science: Biomedical Technology; Clinical Medicine; Surgery and Transplantation, 7, 221 (1979).
Svedman, "A Dressing System Providing Fluid Supply and Suction Drainage Used for Continuous or Intermittent Irrigation," Annals of Plastic Surgery, vol. 17, No. 2, Aug. 1986 (125-133).
Svedman, "Irrigation Treatment of Leg Ulcers," The Lancet, Sep. 3, 1983 (532-534).
Svedman, et al., "Staphylococcal Wound Infection in the Pig: Part I. Course," Annals of Plastic Surgery, vol. 23, No. 3, Sep. 1989 (212-218).
Teder, et al., "Continuous Wound Irrigation in the Pig," Journal of Investigative Surgery, vol. 3 (399-407).
Usupov, et al., "Active Wound Drainage," Russian Journal: Vestnik Khirugii, 1987, Apr. (42-45).
Yu A. Davydov, et al., "Bacteriological and Cytological Assessment of Vacuum Therapy of Purulent Wounds", Vestnik Khirurgii, 1988 Oct. 1988, (48-52).
Yu A. Davydov, et al., "Concepts for Clinical Biological Management of the Wound Process in the Treatment of Purulent Wounds Using Vacuum Therapy," Vestnik Khirugii, Feb. 1991, (32-135).

(56) References Cited

OTHER PUBLICATIONS

Yu A. Davydov, et al., "Vacuum Therapy in the Treatment of Purulent Lactation Mastitis," Russian Journal: Vesnik Khirurgii, Sep. 1986, (66-70).

Yu A. Davydov, et al., "Vacuum Therapy in treatment of Acute Purulent Diseases of Soft Tissues and Purulent Wounds," Vestnik Khirurgii, (Surgeon's Herald), Medicine Publishers, 1986.

Aubrey, D.A., et al., Treatment of the Perineal Wound after Proctectomy by Intermittent Irrigation, Arch. Surg., Oct. 1984, 119, 1141-1144.

Bier, A., Hyperemia as a Therapeutic Agent, Ed. Dr. Gustavus M. Blech, A. Robertson & Co., Chicago 1905.

Chardack, et al., "Experimental studies on Synthetic Substitutes for Skin and Their Use in the Treatment of Burns," vol. 155, No. 1 (128-136), 1961.

Edlich, R.F., et al.: "Evaluation of a New, Improved Surgical Drainage System," The American Journal of Surgery, vol. 149, pp. 295-298, Feb. 1985.

Garcia-Rinaldi, R., et al., Improving the Efficiency of Wound Drainage Catheters, Amer. Journ. of Surg., Sep. 1975, 130, 372-373.

Health Technology, Literature R., "Vacuum Assisted Closure Therapy for Wound Care", Health Technology Literature Review (Dec. 2004), 3-59.

Kostiuchenok, B. M., et al., "The Vacuum Effect in the Surgical Treatment of Purulent Wounds", The Kremlin Papers: Perspectives in Wound Care, Russian Journal: Vestnik Khirurgii, BlueSky Publishing, La Costa, California (2004), 3-4.

McLaughlan, James, Sterile Microenvironment for Postoperative Wound Care, The Lancet, pp. 503-504, Sep. 2, 1978.

Morykwas, Michael J., et al., "Vacuum-Assisted Closure: A New Method for Wound Control and Treatment: Animal Studies and Basic Foundation", Ann Plast Surg 1997; 38:553-562 (Dec. 10, 1996).

Renasys EZ System for Negative Wound Therapy, Smith & Nephew announcement, dated Feb. 24, 2009, in 3 pages.

Sames, C.P., Sealing of Wounds with Vacuum Drainage, Br. Med. Journ., Nov. 5, 1977, p. 1223, Correspondence.

Stewart, Joanne, Ph.D., World Wide Wounds—Next generation of products for wound management—2002 (13 pages).

Tribble, David E. M.D., An Improved Sump Drain-Irrigation Device of Simple Construction, Archives of Surgery New York, pp. 511-513, 1972 vol. 105.

Wu, W.S., et al. Vacuum therapy as an intermediate phase in wound closure: a clinical experience, Eur J Past Surg (2000) 23: 174-177.

* cited by examiner

ORIENTATION INDEPENDENT CANISTER FOR A NEGATIVE PRESSURE WOUND THERAPY DEVICE

RELATED APPLICATION

This application is a continuation of U.S. patent application Ser. No. 13/476,255, filed May 21, 2012, which is a continuation of U.S. patent application Ser. No. 12/463,563, filed on May 11, 2009, issued as U.S. Pat. No. 8,251,979. The disclosures of these prior applications are hereby incorporated herein by reference in their entirety.

BACKGROUND

Technical Field

The present disclosure relates generally to treating a wound by applying negative pressure to the wound, and, more specifically, to a canister for use with a negative pressure wound therapy system that is operable in any orientation.

Description of the Related Art

Wound closure involves the migration of epithelial and subcutaneous tissue adjacent the wound towards the center and away from the base of the wound until the wound closes. Unfortunately, closure is difficult with large wounds, chronic wounds or wounds that have become infected. In such wounds, a zone of stasis (i.e. an area in which localized swelling of tissue restricts the flow of blood to the tissues) forms near the surface of the wound. Without sufficient blood flow, the epithelial and subcutaneous tissues surrounding the wound not only receive diminished oxygen and nutrients, but, are also less able to successfully fight microbial infection and, thus, are less able to close the wound naturally. Such wounds have presented difficulties to medical personnel for many years.

Negative pressure wound therapy (NPWT), also known as suction or vacuum therapy, has been used in treating and healing wounds. Application of negative pressure, e.g. reduced or sub-atmospheric pressure, to a localized reservoir over a wound has been found to assist in closing the wound by promoting blood flow to the area, stimulating the formation of granulation tissue, and encouraging the migration of healthy tissue over the wound. Negative pressure may also inhibit bacterial growth by drawing fluids from the wound such as exudates, which may tend to harbor bacteria. This technique has proven particularly effective for chronic or healing-resistant wounds, and is also used for other purposes such as post-operative wound care.

Generally, negative pressure therapy provides for a wound covering to be positioned over the wound to facilitate suction at the wound area. A conduit IS introduced through the wound covering to provide fluid communication to an external vacuum source. Atmospheric gas, wound exudates, or other fluids may thus be drawn from the reservoir through the fluid conduit to stimulate healing of the wound. Exudates drawn from the reservoir may be deposited in a collection canister.

Often, a portable NPWT device is worn by the patient so that the patient may remain ambulatory instead of being confined to a stationary position. While a patient is ambulatory, the portable NPWT device tends to tip or tilt in a multitude of directions. If there are enough exudates in the collection canister, the exudates may cover a suction port leading from the vacuum source to the collection canister because fluid seeks its own level. Covering the suction port prevents the application of negative pressure to the wound thereby discontinuing wound therapy. Additionally, covering the suction port may provide a false indication that the collection canister is full and needs to be replaced when there may be additional space in the canister to fill with exudate.

In addition, portable NPWT devices have a control unit attached to the canister. The control unit generally contains the suction pump and sensitive electronics such as a pressure transducers, microprocessors, or the like. When the NPWT device tips, exudate may aspirate from the canister into the control unit thereby damaging the suction pump and/or electronic components.

SUMMARY

The present disclosure relates to a portable NPWT system including a dressing assembly for positioning over a wound to apply a negative pressure to the wound and a canister assembly. The canister assembly includes a control unit having a vacuum source and a controller and a collection canister in communication with the dressing assembly operable to receive fluid from the wound. The collection canister has a filter assembly having a first filter and a second filter at opposing ends of the collection canister. There is a first passageway between the first filter and a wall of the collection canister and a second passageway between the second filter and a wall of the collection canister. The collection canister also includes a canister interface having a suction port, an inlet port, and a channel. The vacuum source draws air through the suction port from the channel which draws air from the passageway connected to the channel, the air in the passageway is drawn from the collection canister through the filter, and the air in the collection canister is drawn through the inlet port.

The present disclosure also relates to a portable NPWT system including a dressing assembly for positioning over a wound to apply a negative pressure to the wound and a canister assembly. The canister assembly includes a control unit having a vacuum source and a controller and a collection canister in communication with the dressing assembly operable to receive fluid from the wound. The collection canister includes a filter assembly having at least one filter, a passageway between the filter and a wall of the collection canister, and a canister interface having a suction port, an inlet port, and a channel. The vacuum source draws air through the suction port from the channel which draws air from the passageway connected to the channel. The air in the passageway is drawn from the collection canister through the filter and the air in the collection canister is drawn through the inlet port.

BRIEF DESCRIPTION OF THE DRAWINGS

Various embodiments of the wound dressing system of the present disclosure are described herein with reference to the drawings wherein.

DETAILED DESCRIPTION OF THE PREFERRED EMBODIMENTS

Various embodiments of the present disclosure provide negative pressure wound therapy systems (or apparatus) including a collection canister having a chamber to collect wound fluids. Embodiments of the presently disclosed negative pressure wound therapy systems are generally suitable for use in applying negative pressure to a wound to facilitate healing of the wound in accordance with various treatment modalities. Embodiments of the presently disclosed negative pressure wound therapy systems are entirely portable and may be worn or carried by the user such that the user may be completely ambulatory during the therapy period. Embodiments of the presently disclosed negative pressure wound therapy apparatus and components thereof may be entirely reusable or may be entirely disposable after a predetermined period of use or may be individually disposable whereby some of the components are reused for a subsequent therapy application.

Hereinafter, embodiments of the presently disclosed negative pressure wound therapy systems and embodiments of the presently disclosed sensors for use in negative pressure wound therapy systems will be described with reference to the accompanying drawings. Like reference numerals may refer to similar or identical elements throughout the description of the figures. As used herein, "wound exudate", or, simply, "exudate", generally refers to any fluid output from a wound, e.g., blood, serum, and/or pus, etc. As used herein, "fluid" generally refers to a liquid, a gas or both.

Figure 1:
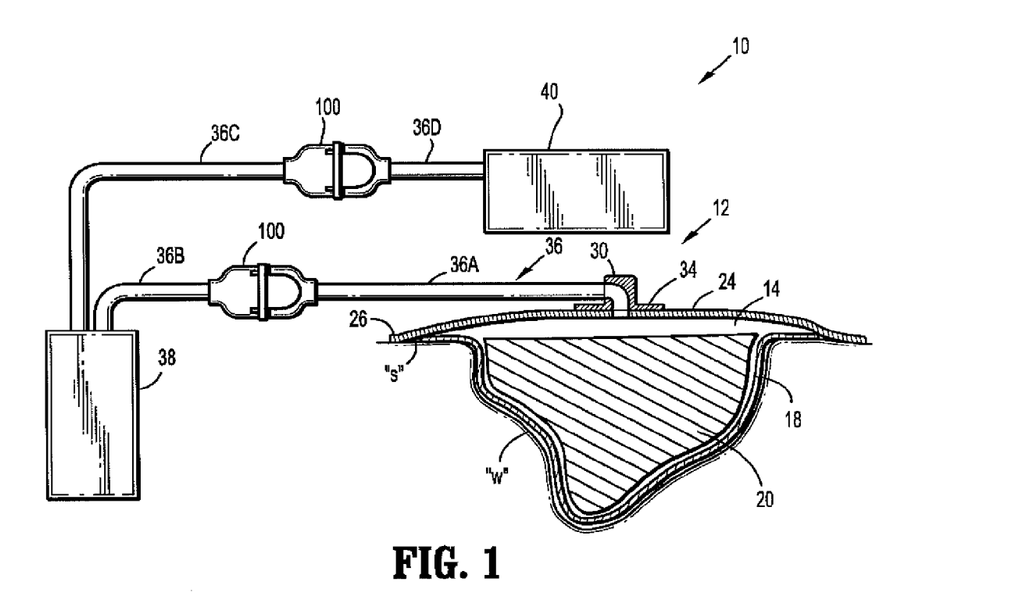
FIG. 1 is a diagram of a NPWT system in accordance with an embodiment of the present disclosure.

Referring to FIG. 1, a negative pressure wound therapy apparatus according to an embodiment of the present disclosure is depicted generally as 10 for use on a wound bed "w" surrounded by healthy skin "s". Negative pressure wound therapy apparatus 10 includes a wound dressing 12 positioned relative to the wound bed "w" to define a vacuum chamber 14 about the wound bed "w" to maintain negative pressure at the wound area. Wound dressing 12 includes a contact layer 18, a wound filler 20 and a wound cover 24.

Contact layer 18 is intended for placement within the wound bed "w" and may be relatively non-supportive or flexible to substantially conform to the topography of the wound bed "w". A variety of materials may be used for the contact layer 18. Contact layer 18 selection may depend on various factors such as the patient's condition, the condition of the periwound skin, the amount of exudate and/or the condition of the wound bed "w". Contact layer 18 may be formed from perforated film material. The porous characteristic of the contact layer 18 permits exudate to pass from the wound bed "w" through the contact layer 18. Passage of wound exudate through the contact layer 18 may be substantially unidirectional such that exudate does not tend to flow back into the wound bed "w". Unidirectional flow may be encouraged by directional apertures, e.g., apertures positioned at peaks of undulations or cone-shaped formations protruding from the contact layer 18. Unidirectional flow may also be encouraged by laminating the contact layer 18 with materials having absorption properties differing from those of the contact layer 18, or by selection of materials that promote directional flow. A nonadherent material may be selected for forming the contact layer 18 such that the contact layer 18 does not tend to cling to the wound bed "w" or surrounding tissue when it is removed. One example of a material that may be suitable for use as a contact layer 18 is commercially available under the trademark XEROFLOW® offered by Tyco Healthcare Group LP (d/b/a Covidien). Another example of a material that may be suitable for use as the contact layer 18 is the commercially available CURITY® non-adherent dressing offered by Tyco Healthcare Group LP (d/b/a Covidien).

Wound filler 20 is positioned in the wound bed "w" over the contact layer 18 and is intended to transfer wound exudate. Wound filler 20 is conformable to assume the shape of any wound bed "w" and may be packed up to any level, e.g., up to the level of healthy skin "s" or to overfill the wound such that wound filler 20 protrudes over healthy skin "s". Wound filler 20 may be treated with agents such as polyhexamethylene biguanide (PHMB) to decrease the incidence of infection and/or other medicaments to promote wound healing. A variety of materials may be used for the wound filler 20. An example of a material that may be suitable for use as the wound filler 20 is the antimicrobial dressing commercially available under the trademark KERLIX™ AMD offered by Tyco Healthcare Group LP (d/b/a Covidien).

Cover layer 24 may be formed of a flexible membrane, e.g., a polymeric or elastomeric film, which may include a biocompatible adhesive on at least a portion of the cover layer 24, e.g., at the periphery 26 of the cover layer 24. Alternately, the cover layer 24 may be a substantially rigid member. Cover layer 24 may be positioned over the wound bed "w" such that a substantially continuous band of a biocompatible adhesive at the periphery 26 of the cover layer 24 forms a substantially fluid-tight seal with the surrounding skin "s". An example of a material that may be suitable for use as the cover layer 24 is commercially available under the trademark CURAFORM ISLAND® offered by Tyco Healthcare Group LP (d/b/a Covidien).

Cover layer 24 may act as both a microbial barrier and a fluid barrier to prevent contaminants from entering the wound bed "w" and to help maintain the integrity thereof.

In one embodiment, the cover layer 24 is formed from a moisture vapor permeable membrane, e.g., to promote the exchange of oxygen and moisture between the wound bed "w" and the atmosphere. An example of a membrane that may provide a suitable moisture vapor transmission rate (MVTR) is a transparent membrane commercially available under the trade name POLYSKIN® II offered by Tyco Healthcare Group LP (d/b/a Covidien). A transparent membrane may help to permit a visual assessment of wound conditions to be made without requiring removal of the cover layer 24.

Wound dressing 12 may include a vacuum port 30 having a flange 34 to facilitate connection of the vacuum chamber 14 to a vacuum system. Vacuum port 30 may be configured as a rigid or flexible, low-profile component and may be adapted to receive a conduit 36 in a releasable and fluid-tight manner. An adhesive on at least a portion of the underside of the flange 34 may be used to provide a mechanism for affixing the vacuum port 30 to the cover layer 24. The relative positions, size and/or shape of the vacuum port 30 and the flange 34 may be varied from an embodiment depicted in FIG. 1. For example, the flange 34 may be positioned within the vacuum chamber 14 such that an adhesive on at least a portion of an upper side surface of the flange 34 affixes the vacuum port 30 to the cover layer 24. A hollow interior portion of the vacuum port 30 provides fluid communication between the conduit 36 and the vacuum chamber 14. Conduit 36 extends from the vacuum port 30 to provide fluid communication between the vacuum chamber 14 and the vacuum source 40. Alternately, the vacuum port 30 may not be included in the dressing 12 if other provisions are made for providing fluid communication with the conduit 36.

Any suitable conduit may be used for the conduit 36, including conduit fabricated from flexible elastomeric or polymeric materials. In the negative pressure wound therapy apparatus 10 illustrated in FIG. 1, the conduit 36 includes a first conduit section 36A, a second conduit section 36B, a third conduit section 36C and a fourth conduit section 36D. The first conduit section 36A extends from the vacuum port 30 and is coupled via a fluid line coupling 100 to the second conduit section 36B, which extends to the collection canister 38. The third conduit section 36C extends from the collection canister 38 and is coupled via another fluid line coupling 100 to the fourth conduit section 36D, which extends to the vacuum source 40. The shape, size and/or number of conduit sections of the conduit 36 may be varied from the first, second, third and fourth conduit sections 36A, 36B, 36C and 36D depicted in FIG. 1.

The first, second, third and fourth conduit sections 36A, 36B, 36C and 36D of the conduit 36 may be connected to components of the apparatus 10 by conventional air-tight means, such as, for example, friction fit, bayonet coupling, or barbed connectors. The connections may be made permanent. Alternately, a quick-disconnect or other releasable connection means may be used to provide some adjustment flexibility to the apparatus 10.

Collection canister 38 may be formed of any type of container that is suitable for containing wound fluids. For example, a semi-rigid plastic bottle may be used for the collection canister 38. A flexible polymeric pouch or other hollow container body may be used for the collection canister 38. Collection canister 38 may contain an absorbent material to consolidate or contain the wound fluids or debris. For example, super absorbent polymers (SAP), silica gel, sodium polyacrylate, potassium polyacrylamide or related compounds may be provided within collection canister 38. At least a portion of canister 38 may be transparent or semi-transparent, e.g., to permit a visual assessment of the wound exudate to assist in evaluating the color, quality and/or quantity of exudate. A transparent or semi-transparent portion of the collection canister 38 may permit a visual assessment to assist in determining the remaining capacity or open volume of the canister and/or may assist in determining whether to replace the collection canister 38.

The collection canister 38 is in fluid communication with the wound dressing 12 via the first and second conduit sections 36A, 36B. The third and fourth conduit sections 36C, 36D connect the collection canister 38 to the vacuum source 40 that generates or otherwise provides a negative pressure to the collection canister 38. Vacuum source 40 may include a peristaltic pump, a diaphragmatic pump or other suitable mechanism. Vacuum source 40 may be a miniature pump or micropump that may be biocompatible and adapted to maintain or draw adequate and therapeutic vacuum levels. The vacuum level of subatmospheric pressure achieved may be in the range of about 20 mmHg to about 500 mmHg. In embodiments, the vacuum level may be about 75 mmHg to about 125 mmHg, or about 40 mmHg to about 80 mmHg. One example of a peristaltic pump that may be used as the vacuum source 40 is the commercially available KANGAROO PET™ Enteral Feeding Pump offered by Tyco Healthcare Group LP (d/b/a Covidien). Vacuum source 40 may be actuated by an actuator (not shown) which may be any means known by those skilled in the art, including, for example, alternating current (AC) motors, direct current (DC) motors, voice coil actuators, solenoids, and the like. The actuator may be incorporated within the vacuum source 40.

In embodiments, the negative pressure wound therapy apparatus 10 includes one or more fluid line couplings 100 that allow for selectable coupling and decoupling of conduit sections. For example, a fluid line coupling 100 may be used to maintain fluid communication between the first and second conduit sections 36A, 36B when engaged, and may interrupt fluid flow between the first and second conduit sections 36A, 36B when disengaged. Thus, fluid line coupling 100 may facilitate the connection, disconnection or maintenance of components of the negative pressure wound therapy apparatus 10, including the replacement of the collection canister 38. Additional or alternate placement of one or more fluid line couplings 100 at any location in line with the conduit 36 may facilitate other procedures. For example, the placement of a fluid line coupling 100 between the third and fourth conduit sections 36C, 36D, as depicted in FIG. 1, may facilitate servicing of the vacuum source 40.

Figure 2:
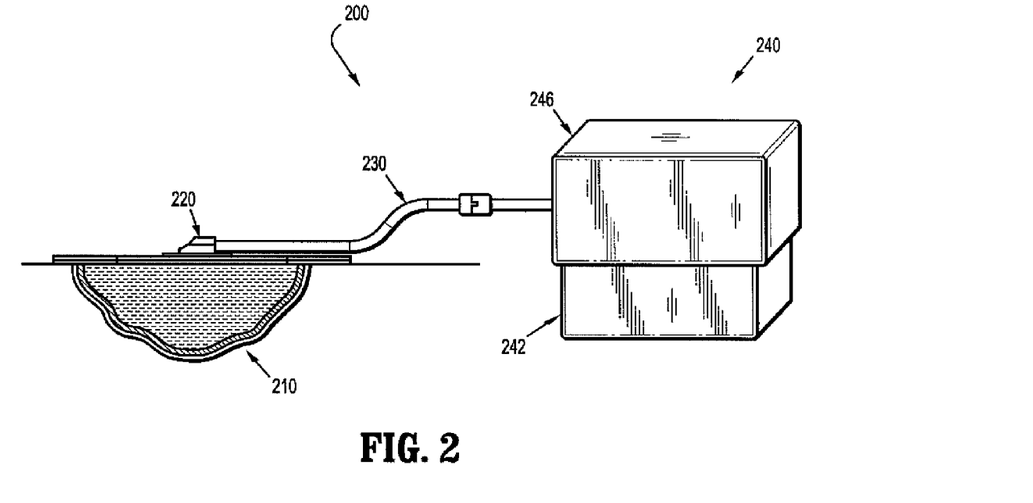
FIG. 2 is a diagram of a NPWT system in accordance with an embodiment of the present disclosure.

Referring to FIG. 2, the negative pressure wound therapy system shown generally as 200 includes a dressing assembly 210, a wound port assembly 220, an extension assembly 230 and a canister assembly 240. Dressing assembly 210 is positioned relative to the wound area to define a vacuum chamber about the wound area to maintain negative pressure at the wound area. Dressing assembly 210 may be substantially sealed from extraneous air leakage, e.g., using adhesive coverings. Wound port assembly 220 is mounted to the dressing assembly 210. For example, wound port assembly 220 may include a substantially continuous band of adhesive at its periphery for affixing the wound port assembly 220 to the dressing assembly 210. Extension assembly 230 is coupled between the wound port assembly 220 and the canister assembly 240 and defines a fluid flow path between the wound port assembly 220 and the canister assembly 240. A hollow interior of the wound port assembly 220 provides fluid communication between the extension assembly 230 and the interior of the dressing assembly 210. Dressing assembly 210 and the wound port assembly 220 shown in FIG. 2 are similar to components of the wound dressing 12 of FIG. 1 and further description thereof is omitted in the interests of brevity.

Canister assembly 240 includes a control unit 246 and a collection canister 242 disposed below the control unit 246. Control unit 246 and the collection canister 242 may be releasably coupled. Mechanisms for selective coupling and decoupling of the control unit 246 and the collection canister 242 include fasteners, latches, clips, straps, bayonet mounts, magnetic couplings, and other devices. Collection canister 242 may consist of any container suitable for containing wound fluids.

In one embodiment, the negative pressure wound therapy system 200 is capable of operating in a continuous mode or an alternating mode. In the continuous mode, the control unit 246 controls a pump to continuously supply a selected vacuum level at the collection canister 242 to create a reduced pressure state within the dressing assembly 210. In the alternating mode, the control unit 246 controls the pump to alternating supply a first negative pressure, e.g., about 80 mmHg, at the collection canister 242 for a preset fixed amount of time and a second negative pressure, e.g., about 50 mmHg, at the collection canister 242 for a different preset fixed amount of time.

In general, the output of the pump is directly related to the degree of air leakage in the negative pressure wound therapy system 200 and the open volume in the collection canister 242. If there is sufficient air leakage in the system 200, e.g., at the dressing assembly 210, the pump can remain on continuously and the control unit 246 can control negative pressure at the collection canister 242 by adjusting the pump speed. Alternatively, if there is not sufficient air leakage in the system 200 to permit the pump to remain on continuously, the control unit 246 can control negative pressure at the collection canister 242 by turning the pump on and off, e.g., for non-equal on/off periods of time.

Control unit 246 responds to various sensed events by signaling alarms. Various types of conditions may be signaled by alarms. In embodiments, control unit 246 is capable of signaling alarms for failed pressure sensor condition, use odometer expired condition, watchdog reset condition, failed pump condition, leak condition, replace canister condition, excessive vacuum condition, failed LEDs condition, low battery condition, very low battery condition, and failed battery condition. Priority levels may be associated with alarms. In embodiments, the priority levels of alarms are low priority alarm, medium priority alarm, and system alarm (highest priority). Low priority alarms, when triggered, may be continuously indicated. Medium priority alarms and system alarms, when triggered, may have a flashing indication.

Control unit 246 may stop operation of the in response to an alarm, e.g., depending on alarm type and/or priority level. In embodiments, the control unit 246 stops operation of the pump in response to system alarms, e.g., failed pressure sensor system alarm, use odometer expired system alarm, watchdog reset system alarm, failed pump system alarm, excessive vacuum system alarm, and/or failed LEDs system alarm.

If an air leak develops in the negative pressure wound therapy system 200, e.g., at the dressing assembly 210, for which the control unit 246 cannot compensate by increasing the pump speed, the control unit 246 may indicate an alarm. For example, the control unit 246 may indicate a leak alarm after two consecutive minutes of operation in which the vacuum level is below the current set point (or below the minimum level of a set point range).

Audible indicatory means may also be incorporated or associated with the control unit 246 to notify the user of a condition, e.g., leak, canister assembly tip, failed pressure sensor, failed pump, excessive vacuum, or low battery conditions. The audio indication for some alarm types can be paused by pressing a pause alarm button (not shown).

In embodiments, the control unit 246 includes a user interface (not shown). Control unit 246 also includes a processor. A pressure transducer is electrically coupled to the processor. The user turns ON the canister assembly 240 by pressing a power button (not shown). When the power button is pressed, the control unit 246 performs a series of internal checks during power up. In one embodiment, after successfully completing the power-up tasks, the control unit 246 turns on the pump 360 using the stored settings. At initial activation of the canister assembly 240, the stored settings are the default settings. In one embodiment, the default settings for controlling the pump 360 are 80 mmHg and continuous mode. In one embodiment, the currently stored vacuum level setting can be altered by the user, e.g., to 50 mmHg. In one embodiment, the currently stored mode setting can be altered by the user, e.g., to an alternating mode.

Canister assembly 240 may be constructed from a variety of materials such as Lucite™ polycarbonate, metals, metal alloys, plastics, or other durable materials capable of withstanding forces applied during normal use, and may have some capability of withstanding possibly excessive forces resulting from misuse. Collection canister 242 may include a window with fluid level markings or for promoting visual assessment of the amount of exudate contained within the collection canister 242. A transparent or partially transparent collection canister 242 may thus assist in determining the remaining capacity of the collection canister 242 and/or when the collection canister 242 should be replaced.

Figure 3:
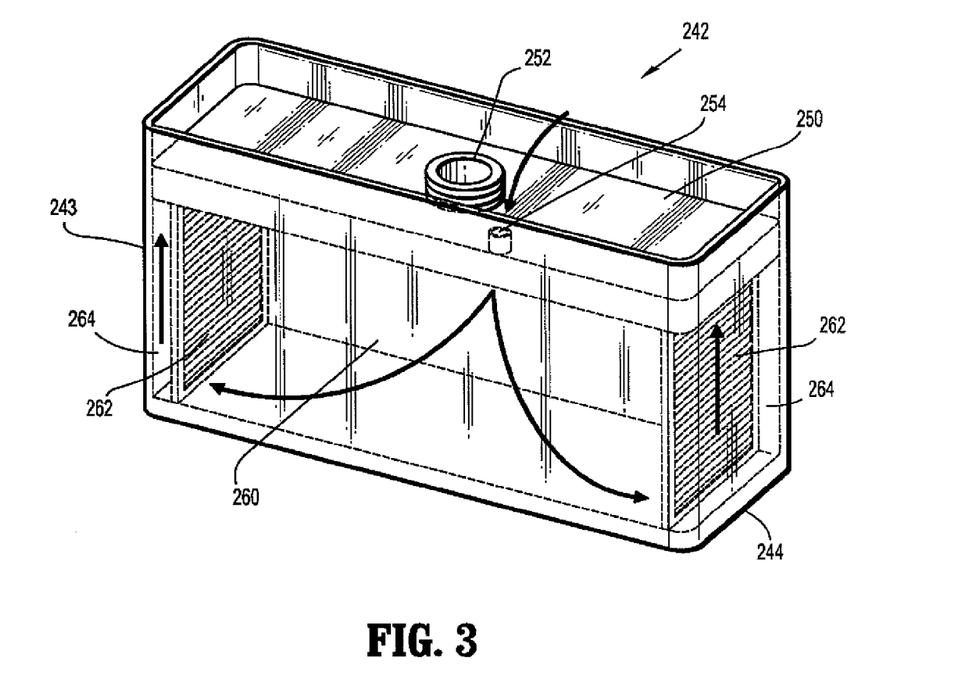
FIG. 3 is a diagram of a canister for a NPWT system in accordance with an embodiment of the present disclosure.

Referring to FIG. 3, a collection canister, shown generally as 242, in accordance with an embodiment of the present disclosure is shown. The collection canister 242 has a canister interface 250 with a suction port 252 and an inlet port 254. Inlet port 254 receives exudate from the wound "w" through the wound port assembly 220 and extension assembly 230. Suction port 252 is coupled to a pump (not shown) in control unit 246. Exudate is collected in chamber or space 260 of the canister 242.

Collection canister 242 also includes a pair of filters 262 on opposing sides of the collection canister 242. Although FIG. 3 shows the filters 262 parallel to the left wall 243 and right wall 244 of the collection canister 242, filters 262 may also be placed parallel to the front and rear walls of the collection canister 242. Filter 262 may be a hydrophobic or oleophobic filter to prevent exudate from exiting the canister. Filter 262 may be a replaceable cartridge that can be replaced during a canister change. Filter 262 may also include an antibacterial coating. Although not shown, an odor filter such as a charcoal filter may also be placed in line with filter 262 to reduce odor produced by exudate. Between filter 262 and the left wall 243 or right wall 244 is a fluid path or passageway 264.

Figure 4:
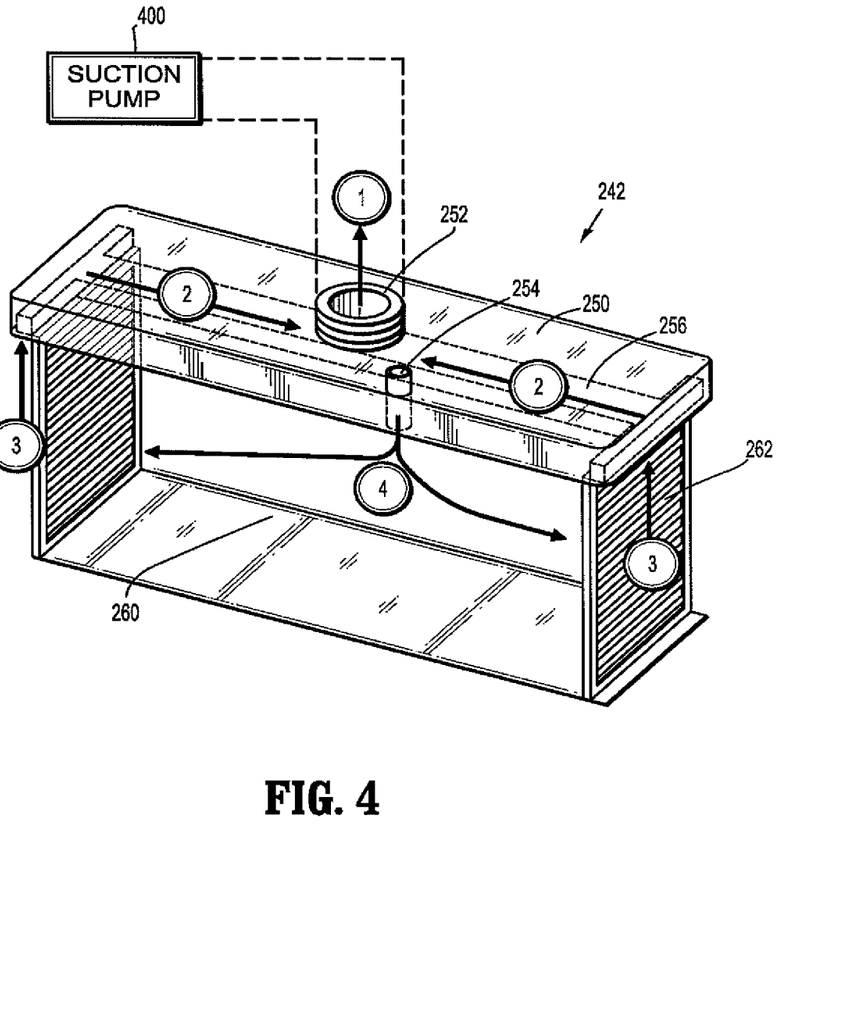
FIG. 4 is a diagram of a canister for a NPWT system in accordance with an embodiment of the present disclosure.

During operation of the NPWT device, the suction pump 400 (as shown in FIG. 4) draws air through suction port 252 in canister interface 250. This causes air to be drawn up passageways 264 from chamber 260 through filters 262. Filters 262 prevent exudate from entering passageway 264 while allowing air to pass through. Drawing air from chamber 260 into passageways 264 imparts a negative pressure in chamber 260 thereby causing air and/or exudate to collect in chamber 260 via inlet port 254.

Referring to FIG. 4, canister 242 is depicted without the external walls of canister 242 and canister interface 250 to show the movement of air within canister 242. FIG. 4 depicts four stages of air movement through the canister. As previously described, suction pump 400 draws in air from suction port 252 as shown in stage 1. In stage 2, air is drawn through channel 256 to the suction port 252. Channel 256 extends from the left side to the right side of the canister interface 250. Below channel 256 along the left edge and the right edge of the canister interface are passageways 264 of FIG. 3. In stage 3, air is drawn from passageways 264 to channel 256. Air in passageways 264 is drawn from chamber 260 as shown in stage 4.

The canister 242 shown in FIGS. 3 and 4 depict an embodiment according to the present disclosure that enables a NPWT device to continue functioning if the canister assembly has been tipped, tilted or inverted. If the canister assembly is tipped or tilted toward the left wall 243 thereby covering the filter 262 on the left wall 243, air is continuously drawn through filter 262 on the right wall 244. Because air is still drawn through the filter 262 along the right wall 244, the NPWT device can maintain a negative or reduced pressure in the chamber 260 thereby maintaining a negative or reduced pressure at the wound "w". The same holds true if the canister is tipped toward the right wall 244 because the filter 262 along the left wall 243 will remain uncovered. If the canister assembly is inverted, air will still be drawn through filters 262 where exudate has not covered the filters 262. Also, because the suction port 252 is isolated from the chamber 260 where exudate is present by filter 262, passageway 264 and channel 256, exudate cannot enter the control unit 246 thereby damaging the electronics therein.

Figures 5A, 5B:
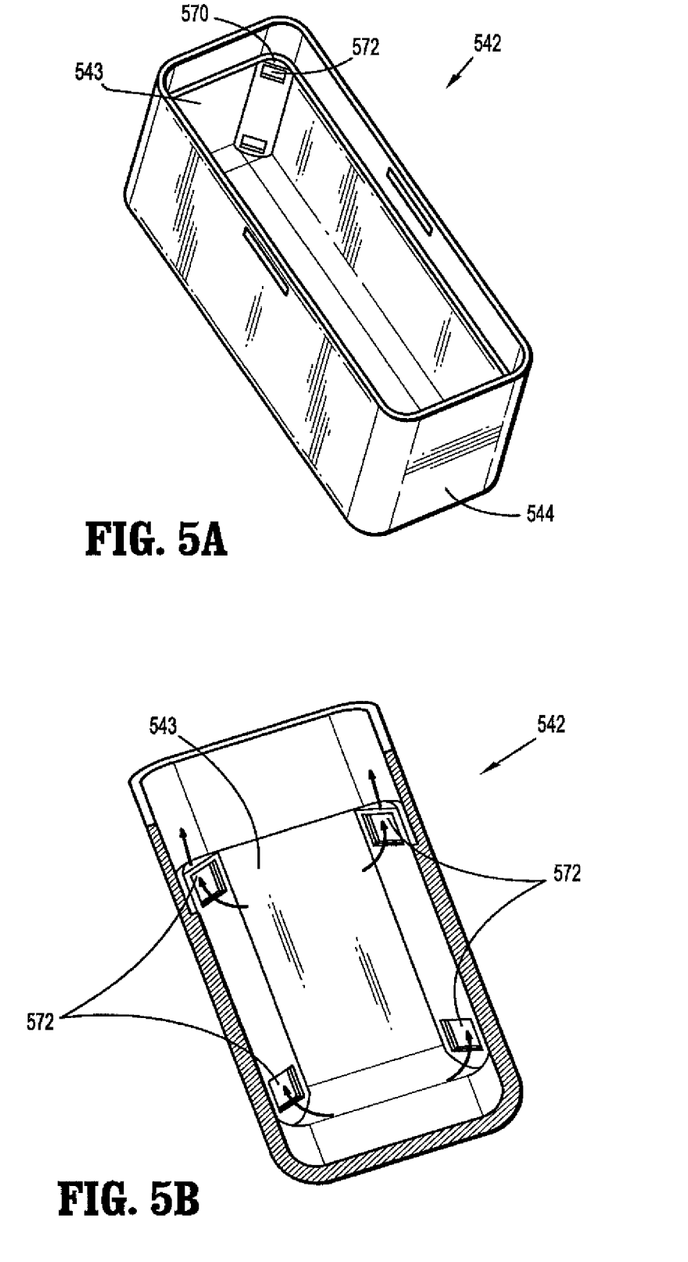
FIG. 5A is a diagram of a canister for a NPWT system in accordance with an embodiment of the present disclosure.
FIG. 5B is a diagram of a canister for a NPWT system in accordance with an embodiment of the present disclosure.

FIGS. 5A and 5B depict another embodiment according to the present disclosure. In FIG. 5A, canister 542 is shown without a canister interface. FIG. 5B is a cross sectional view of canister 542 shown in FIG. 5A. As shown in FIG. 5B, canister 542 has a left wall 543 with four filters generally shown as 572 located substantially at the corners of the left wall 543. Each filter 572 may have one or more filters that may be hydrophobic or oleophobic. Filter 572 leads to a passageway 570 as shown in FIG. 5A. Although FIG. 5B depicts the left wall having four filters, right wall 544 also has similar filters at its corners. As such, the canister 542 has filters located at the eight vertices of the canister 542. Passageway 570 leads to a canister interface (not shown) which has a suction port (not shown) leading to the suction pump (not shown). It is to be appreciated by one skilled in the art that the canister interface for canister 542 may be substantially similar to the canister interface 250 shown in FIG. 4. Unless the canister 542 is completely full of said exudate, one or more of filters 572 located at the eight vertices will not be covered by exudate even when the canister 542 is tipped, tilted, or inverted. Canister 542 allows the canister assembly 240 to be tipped or tilted in any direction while maintaining a negative or reduced pressure at the wound "w".

Figure 6:
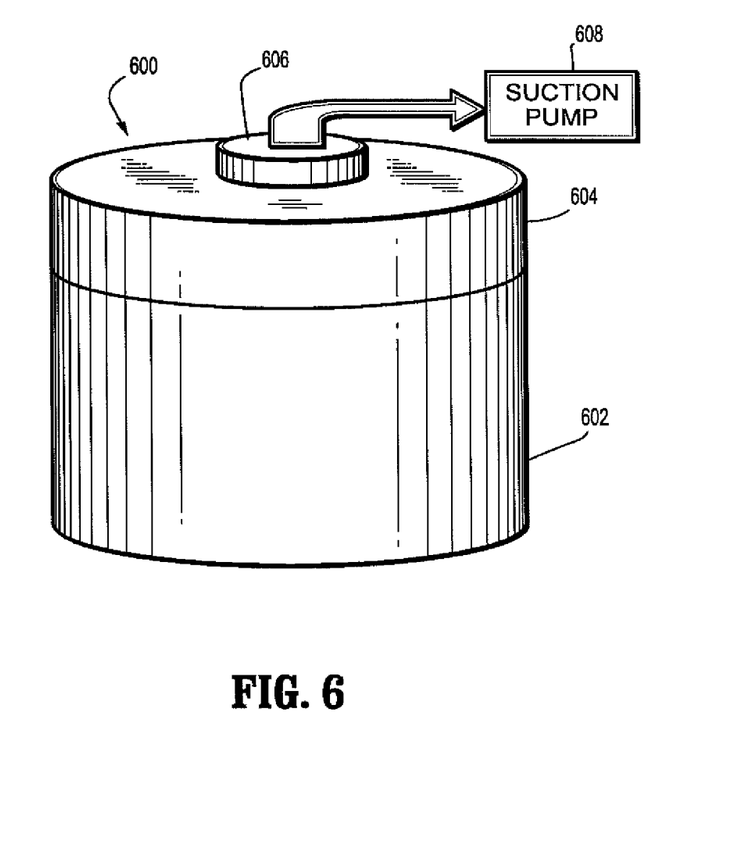
FIG. 6 is a diagram of a canister assembly for an NPWT system in accordance with an embodiment of the present disclosure.

FIG. 6 depicts another embodiment according to the present disclosure. As shown in FIG. 6, a substantially round canister assembly 600 is shown. The base of canister assembly 600 may be circular, oval or elliptical in shape. Canister assembly has a canister 602 a canister interface 604 and a suction port 606. Air is drawn through the suction port 606 by suction pump 608 thereby imparting a negative or reduced pressure in canister 602.

Figure 7A:
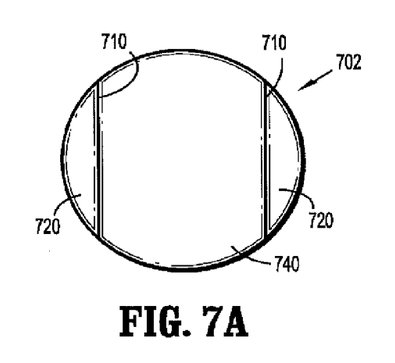
FIG. 7A is a top view of a canister for a NPWT system in accordance with an embodiment of the present disclosure.
Figure 7B:
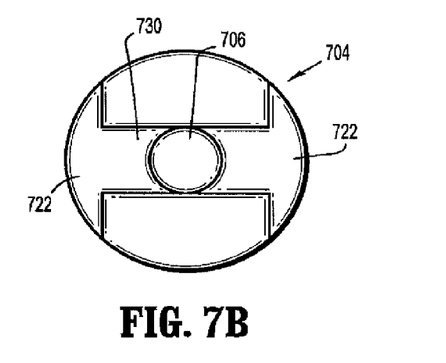
FIG. 7B is a top view of a canister interface for a NPWT system in accordance with an embodiment of the present disclosure.

FIGS. 7B and 7B depict top views of the canister and canister interface of FIG. 6 in accordance with an embodiment of the present disclosure. As shown in FIG. 7A, canister 702 has two filters 710, which are substantially similar to the filters described above, that are parallel to each other. Each filter 710 leads to a passageway 720 which leads to the canister interface 704 shown in FIG. 7B. Canister interface 704 has channels 722 which are positioned over passageways 720 of canister 702. Channels 722 lead to central channel 730 which leads to suction port 706. Suction pump 608 (as shown in FIG. 6) draws air through suction port 706 which then draws air through central channel 730. Air is drawn through central channel 730 from channels 722 and passageways 720. Such action causes air to be drawn through filters 710 thereby imparting a negative pressure in chamber 740 of canister 702.

Figure 8A:
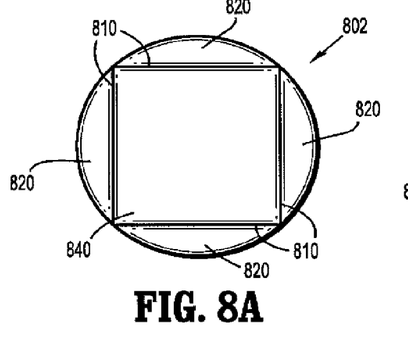
FIG. 8A is a top view of a canister for a NPWT system in accordance with an embodiment of the present disclosure.
Figure 8B:
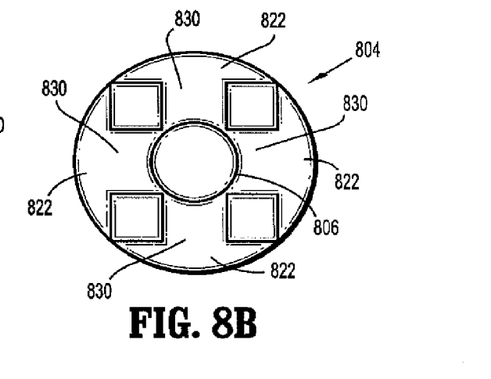
FIG. 8B is a top view of a canister interface for a NPWT system in accordance with an embodiment of the present disclosure.

FIGS. 8A and 8B depict top views of the canister and canister interface of FIG. 6 in accordance with an embodiment of the present disclosure. As shown in FIG. 8A, canister 802 has filter assembly 810 that are substantially similar to the filters described above. Filter assembly 810 has two pairs of filters with one pair of filters being perpendicular to the other pair of filters as shown in FIG. 8A. Each filter in filter assembly 810 leads to a passageway 820 which leads to the canister interface 804 shown in FIG. 8B. Canister interface 804 has four channels 822 which are positioned over passageways 820 of canister 802. Channels 822 lead to central channel 830 which leads to suction port 806. Suction pump 608 (as shown in FIG. 6) draws air through suction port 806 which then draws air through central channel 830. Air is drawn through central channel 830 from channels 822 and passageways 820. Such action causes air to be drawn through filter assembly 810 thereby imparting a negative pressure in chamber 840 of canister 802.

Figure 9A:
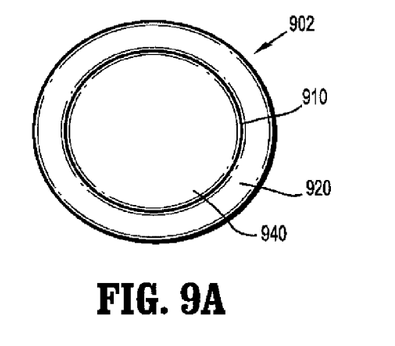
FIG. 9A is a top view of a canister for a NPWT system in accordance with an embodiment of the present disclosure.
Figure 9B:
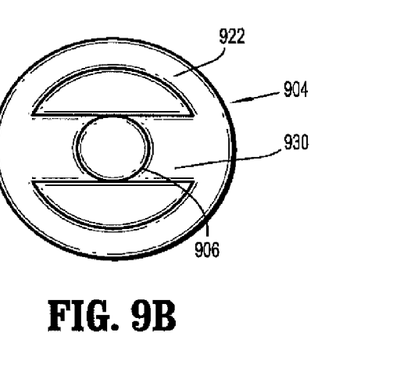
FIG. 9B is a top view of a canister interface for a NPWT system in accordance with an embodiment of the present disclosure.

FIGS. 9A and 9B depict top views of the canister and canister interface of FIG. 6 in accordance with an embodiment of the present disclosure. As shown in FIG. 9A, canister 902 has a filter assembly 910 that is substantially similar to the filters described above. Filter assembly 910 has a substantially similar shape as the canister. Filter assembly 910 leads to a passageway 920 which leads to the canister interface 904 shown in FIG. 9B. Canister interface 904 has channel 922 which is positioned over passageway 920 of canister 902. Channels 922 lead to central channel 930 which leads to suction port 906. Suction pump 608 (as shown in FIG. 6) draws air through suction port 906 which then draws air through central channel 930. Air is drawn through central channel 930 from channel 922 and passageway 920. Such action causes air to be drawn through filter assembly 910 thereby imparting a negative pressure in chamber 940 of canister 902.

While the disclosure has been illustrated and described, it is not intended to be limited to the details shown, since various modifications and substitutions can be made without departing in any way from the spirit of the present disclosure. As such, further modifications and equivalents of the invention herein disclosed can occur to persons skilled in the art using no more than routine experimentation, and all such modifications and equivalents are believed to be within the spirit and scope of the disclosure as defined by the following claims.

What is claimed is:

1. A portable negative pressure wound therapy system comprising:
　a collection canister configured to be in communication with a dressing and configured to receive fluid removed from a wound, the collection canister comprising:
　　a first chamber comprising an inlet port configured to be in fluid communication with the dressing and further configured to allow fluid removed from the wound to flow into the first chamber, wherein the first chamber comprises a plurality of walls; and
　　a second chamber comprising a plurality of passageways or channels, the second chamber comprising a negative pressure port configured to be in fluid communication with a negative pressure source, the second chamber comprising a plurality of walls and a plurality of filters in fluid communication with the negative pressure port;

wherein the second chamber comprises a first passageway and second passageway from the plurality of passageways or channels, wherein the first and second passageway are configured to allow fluid communication between the first chamber and the second chamber, the first and second passageways located on different walls of the first chamber;

wherein the first chamber comprises a first filter and a second filter from the plurality of filters, wherein the first and second filters are located on different walls of the first chamber; and wherein the first and second passageways are configured to impart negative pressure to the first chamber in the event one of the first or second passageway becomes occluded such that when one of the first or second passageways becomes occluded, negative pressure is applied to the first chamber through the other passageway.

2. The portable negative pressure wound therapy system of claim 1, wherein the dressing is configured to be placed over the wound.

3. The portable negative pressure wound therapy system of claim 1, further comprising a control unit having the negative pressure source and a controller.

4. The portable negative pressure wound therapy system of claim 1, wherein the plurality of filters are hydrophobic or oleophobic.

5. The portable negative pressure wound therapy system of claim 1, wherein the collection canister has at least one passageway associated with the plurality of filters.

6. The portable negative pressure wound therapy system of claim 1, wherein the first and second passageways are located on walls of the second chamber that are parallel to each other.

7. The portable negative pressure wound therapy system of claim 1, wherein the first and second passageways are located substantially at the corners of the walls of the second chamber.

8. The portable negative pressure wound therapy system of claim 1, wherein the first and second passageways are located on walls of the second chamber that are perpendicular to each other.

9. The portable negative pressure wound therapy system of claim 1, further comprising the dressing.

10. The portable negative pressure wound therapy system of claim 1, wherein the different walls of the first chamber comprise opposite walls.

* * * * *